Sept. 18, 1951 H. A. M. VERSCHUREN Plant Pat. 1,038
ROSE PLANT
Filed July 18, 1950
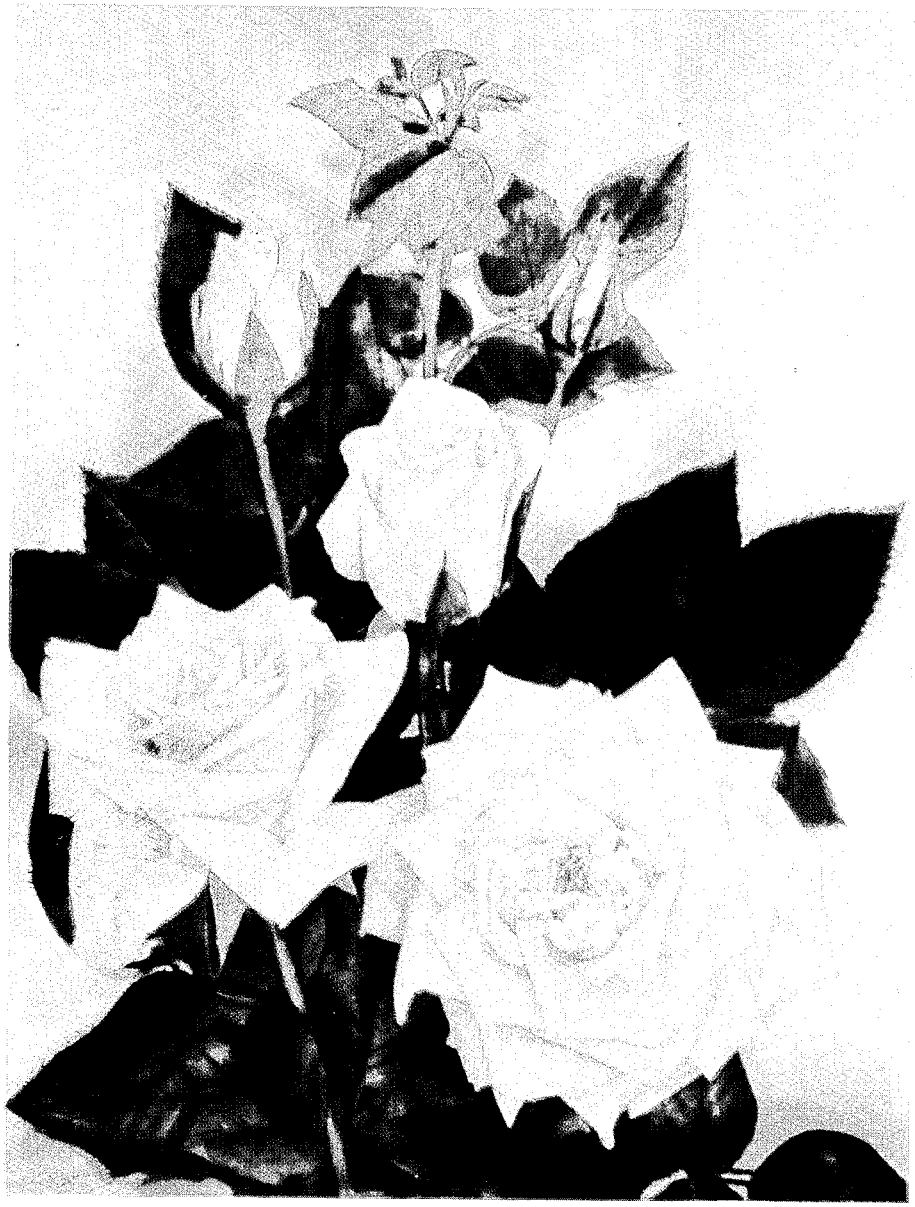
Inventor.
H. A. M. Verschuren
By: Robb & Robb
Attorneys.

Patented Sept. 18, 1951

Plant Pat. 1,038

UNITED STATES PATENT OFFICE 1,038

ROSE PLANT

Hendrikus Antonie Maria Verschuren, Haps, Netherlands, assignor to Jackson & Perkins Company, Newark, N. Y., a corporation of New York Application July 18, 1950, Serial No. 174,549

1 Claim. (Cl. 47—61)

This invention relates to a new and distinct variety of rose plant of the hybrid tea class, originated by crossing the variety "Lady Sylvia" (unpatented × an unnamed and unpatented orange-colored seedling of unknown parentage.

The primary objective of this cross was to obtain better colored and larger flowers on the vigorous bushes of the parents, as well as more continuous blooming of the flowers. This objective was fully achieved in this new variety, as evidenced by the following unique combination of characteristics resulting from the aforementioned cross:

(1) The distinctive color of the flowers which may be generally described as La France Pink, overcast with Shrimp Pink;

(2) The large size and numerous petals of the flowers, the number of petals being almost twice as many as those of the flowers of "Lady Sylvia";

(3) The more vigorous habit of growth of the plant; and (4) The more continuous blooming habit of the plant, which, unlike the Butterfly type of rose, such as the parent "Lady Sylvia," does not stop blooming in December and January, but continues blooming throughout the entire year.

Asexual reproduction of this new variety by budding at Newark, New York, and at Pleasanton, California, shows that the foregoing characteristics come true to form and are established and transmitted through succeeding propagations.

The accompanying drawing shows specimens of the new variety, with the flowers and foliage in different stages of development.

The following is a detailed description of the new variety, with color terminology in accordance with Ridgway's Color Standards and Nomenclature:

Parentage: Seedling.

*Seed parent.*—"Lady Sylvia."

*Pollen parent.*—An unnamed orange-colored seedling of unknown parentage.

Classification: Botanic and commercial—hybrid tea.

*Flower*

(Observations made in greenhouse at Newark, New York, in mid-afternoon early in the month of January, 1950.)

Blooming habit: Recurrent—continuous.

Bud:

*Size.*—Large.

*Form.*—Ovoid. Is not affected by wet or hot weather.

*Color.*—When sepals first divide—Begonia Rose, Plate 1. When petals begin to unfurl—Geranium Pink, Plate 1. When half blown—inside of petals: Grenadine Pink, Plate 2, overcast with La France Pink, Plate 1, and with light Orange Yellow Plate 3, overcasting the lower half of the petal from the base; reverse of petals: Bittersweet Pink, Plate 2, lightening to Shrimp Pink, Plate 1, in the center of the petal, with Light Cadmium, Plate 4, overcasting the lower half of the petal from the base.

*Sepals.*—Slightly branched. Curl back when petals begin to unfurl. Color—inside: Kildare Green, Plate 31; outside: Light Bice Green, Plate 17.

*Calyx.*—Shape—pear. Size—small. Aspect—smooth. Odor when rubbed—none. Color—Parrot Green, Plate 6.

*Peduncle.* — Length — medium. Aspect — rough. Color — Oil Green, Plate 5. Strength—erect; slender.

*Opening.*—Bud opens up well. Is not affected by adverse weather conditions.

Bloom:

*Size.*—Large. Average size when fully expanded, 4½ inches to 5½ inches.

*Borne.*—Singly and several together.

*Stems.*—Medium length; strong.

*Form.*—When first open—high center. Permanence—outer petals curl back.

*Petalage.*—Double (full but open center). Number of petals under normal conditions, 30 to 35.

*Color.*—Center of flower—Thulite Pink, Plate 26, lightly overcast with Orient Pink, Plate 2. Outer petals—La France Pink, Plate 1. Base of petals (aiglet)—Lemon Chrome, Plate 4. Inside of petals—La France Pink, Plate 1, overcast with Shrimp Pink, Plate 1, with a shading of Maize Yellow, Plate 4, overcasting the lower half of the petal. Reverse of petals—Thulite Pink, Plate 26, at the outer edges of the petal, lightening to La France Pink, Plate 1, in the center of the petal, with a shading of Maize Yellow, Plate 4, overcasting the lower half of the petal. General tonality from a distance—Orient Pink, Plate 1, overcast with Shrimp Pink, Plate 1.

*Discoloration.*—General tonality at end of first day—Thulite Pink, Plate 26, lightly overcast with Orient Pink, Plate 2. Second day—La France Pink, Plate 1, lightly overcast with Shrimp Pink, Plate 1. Third day—Shrimp Pink, Plate 1.

Petals:

*Texture.*—Thick. Is not affected by wet or hot weather.

*Appearance.*—Inside—satiny; outside—shiny.

*Form.*—Round.

*Arrangement.*—Imbricated (regularly arranged shinglelike). Petaloids in center—few; large.

*Persistence.*—Drop off cleanly.

*Fragrance.*—Slight. Nature—tea (average hybrid tea scent).

*Lasting quality.*—On the plant and as cut flower—long.

Genital organs:

*Stamens, anthers.*—Medium size; many. Color—Deep Chrome, Plate 3. Arrangement—regular around styles.

*Stamens, filaments.* — Medium length. Color—Pale Lemon Yellow, Plate 4.

*Pollen.*—Color—Martius Yellow, Plate 4.

*Styles.*—Bunched, uneven length; medium length; thin.

*Stigmas.*—Color—Maize Yellow, Plate 4.

*Ovaries.*—All enclosed in calyx.

*Plant*

Form: Bush.

Growth: Vigorous; branching.

Foliage: 3 to 5 leaflets.

*Size.*—Medium.

*Quantity.*—Normal.

*Color.*—New foliage—upper side: Lettuce Green, Plate 5; serrations Oxblood Red, Plate 1; under side: Cosse Green, Plate 5, lightly overcast with Oxblood Red, Plate 1. Old foliage—upper side: Forest Green, Plate 17; under side: Light Hellebore Green, Plate 15.

*Shape.*—Oval pointed.

*Texture.*—Upper side—glossy; under side—smooth. Ribs and veins—ordinary.

*Edge.*—Serrated (saw toothed).

*Serration.*—Double; small.

*Leaf stem.*—Color—Saccardo's Olive Green, Plate 16. Under side—rough.

*Stipules.*—Medium length; smooth.

*Disease resistance.*—Resistant.

Wood:

*New wood.*—Color—Cosse Green, Plate 5. Bark—smooth.

*Old wood.*—Color, Bice Green, Plate 17. Bark—smooth.

Thorns:

*Thorns.*—Quantity—on main stalks from base and on laterals from stalk—ordinary. Form—narrow base; medium length; hooked downward. Color when young—Pomegranate Purple, Plate 12. Position—irregular.

*Prickles and short needles.*—None.

I claim:

A new and distinct variety of rose plant of the hybrid tea class, characterized as to novelty by its distinctive color, by the numerous petals of its large-sized flowers, by the vigorous habit of growth of the plant, and by the continuity of bloom throughout the year, substantially as shown and described.

HENDRIKUS ANTONIE MARIA VERSCHUREN.

No references cited.